United States Patent [19]

Harris

[11] Patent Number: 4,855,461

[45] Date of Patent: Aug. 8, 1989

[54] FUNCTIONALIZED OXACALIXARENES, THEIR PREPARATION AND USE IN INSTANT ADHESIVE COMPOSITIONS

[75] Inventor: Stephen J. Harris, Dublin, Ireland

[73] Assignee: Loctite (Ireland) Ltd., Dublin, Ireland

[21] Appl. No.: 145,993

[22] Filed: Jan. 20, 1988

[30] Foreign Application Priority Data

Jan. 21, 1987 [IE] Ireland ................................. 153/87

[51] Int. Cl.$^4$ ................. C07D 313/00; C07D 321/00; C07D 323/00
[52] U.S. Cl. .................................... 549/348; 549/354; 549/397
[58] Field of Search ....................... 549/348, 354, 397

[56] References Cited

U.S. PATENT DOCUMENTS 4,098,717  7/1978  Burkis .................................. 252/331
4,622,414  11/1986  McKervey ........................... 560/61

OTHER PUBLICATIONS

Dhawan and Gutsche, J. Org. Chem., 48, pp. 1536–1539 (1983).
Gutsche et al., J. Am. Chem. Soc., 103, pp. 3782–3792 (1981).
Chem. Abstracts, vol. 79, No. 17, Abst. #105184X.
Chem. Abstracts, vol. 71, No. 25, Abst. 123825W.

*Primary Examiner*—Mary C. Lee
*Assistant Examiner*—Mary S. Howard

*Attorney, Agent, or Firm*—Edward K. Welch, II; Eugene F. Miller

[57] ABSTRACT

Oxacalixarenes of general formula I:

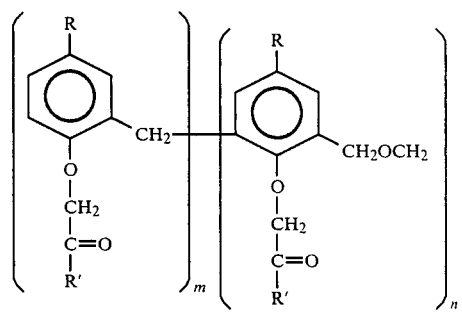

wherein
$m = 0-7$ and $n = 1-8$ with the proviso that $m + n \leq 8$;
R is hydrogen, halogen, or hydrocarbyl, aryl, hydrocarbylaryl or a substituted derivative thereof, and R may be the same or different on each aryl group; and
R' is hydrocarbyl, aryl, hydrocarbylaryl, hydrocarbyloxy, aryloxy or hydrocarbylaryloxy or a substituted derivative thereof.

The invention also provides a method of preparing oxacalixarenes of formula I, and cyanoacrylate adhesive compositions including as accelerator an oxacalixarene of formula I.

7 Claims, No Drawings

FUNCTIONALIZED OXACALIXARENES, THEIR PREPARATION AND USE IN INSTANT ADHESIVE COMPOSITIONS

BACKGROUND OF THE INVENTION

1. Field of the Invention

The present invention relates to etherified oxacalixarenes which are useful for promoting adhesion of cyanoacrylate-based compositions to porous or deactivating surfaces, to a process for their preparation and to adhesive compositions comprising them.

2. Description of the Related Art

Various accelerators have been proposed for improving the curing time of cyanoacrylate-based adhesives on wood, paper or substrates with porous or deactivating surfaces. In general, these adhesive compositions require an accelerator which sequesters alkali metal cations. U.S. Pat. No. 4,171,416 suggests the use of crown ethers, which are macrocyclic molecules capable of complexing with a metallic ion. However, these compounds are highly toxic and therefore unsafe to use.

In U.S. Pat. No. 4,170,585, there are described cyanoacrylate compositions in which certain polyethylene glycols or poly(ethyleneoxy)-functional surfactants act as wood bonding accelerators. Such compounds, however, have the reported disadvantage that they tend to contain water and other difficult to remove substances which spontaneously initiate polymerization of the cyanoacrylate monomer.

U.S. Pat. No. 4,377,490 discloses mixtures of aromatic and aliphatic polyols and polyethers said to improve initial strength of cyanoacrylate wood bonding products.

U.S. Pat. No. 4,386,193 discloses certain 3 or 4 arm polyol podand compounds as alternatives to crown-ether accelerators.

Japan Kokai Tokkyo Koho 82-70171, suggests the use of certain polyorganosiloxane compounds which include polyether substituents as additives for wood bonding cyanoacrylate compositions. Chem. Abstracts, 97 145913n reports the use of a hydroxy-terminated poly(dimethyl-siloxane) in fast bonding cyanoacrylate compositions.

DE-OS No. 3,006,071 discloses certain furan derivatives as co-accelerators with crown ethers in cyanoacrylate compositions.

U.S. Pat. No. 4,556,700 Harris et al describes the use of certain calixarene compounds as accelerators in cyanoacrylate compositions. Irish patent application No. 819/86 Loctite (Ireland) Limited describes further calixarene compounds including polymer-bound calixarene compounds which are also useful for this purpose.

SUMMARY OF THE INVENTION

The present invention provides novel oxacalixarenes of general formula I:

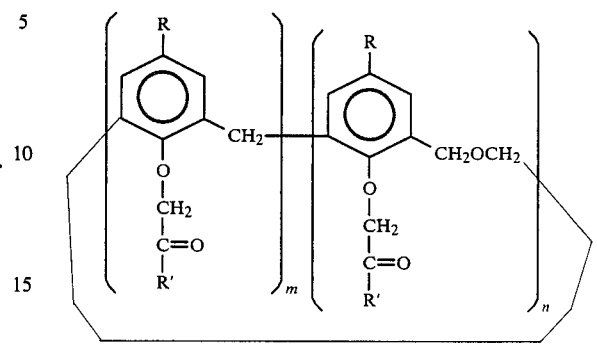

wherein $m=0-7$ and $n=1-8$ with the proviso that $m+n \leq 8$;

R is hydrogen, halogen, or hydrocarbyl, aryl, hydrocarbylaryl or a substituted derivative thereof, and R may be the same or different on each aryl group; and R' is hydrocarbyl, aryl, hydrocarbylaryl, hydrocarbyloxy, aryloxy or hydrocarbylaryloxy or a substituted derivative thereof.

The methyl and ether bridges may or may not alternate within the oxacalixarene molecule.

Preferred etherified oxacalixarenes of formula I are:

(i) an oxacalix-4-arene which has the formula:

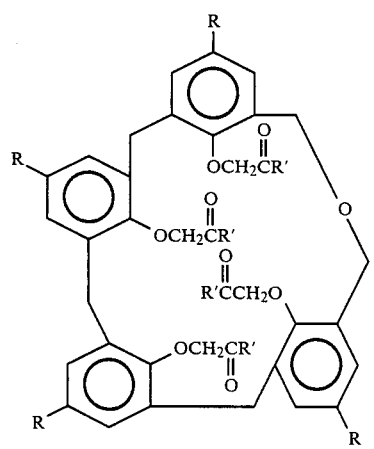

(ii) a dioxacalix-4-arene of formula:

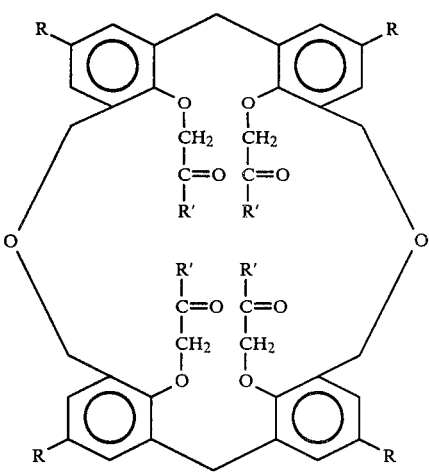

and (iii) a trioxacalix-3-arene of formula:

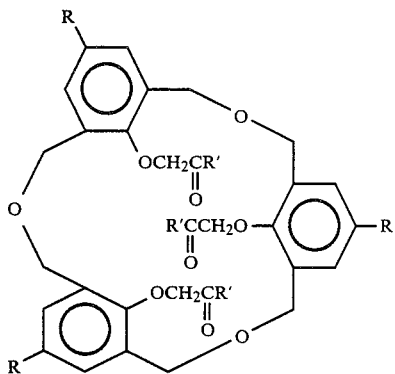

wherein R and R' are as defined above.

In the above compounds, the hydrocarbyl groups shall preferably contain from 1 to 10 carbon atoms, more preferably from 1 to 5 carbon atoms and the aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo groups or substituted or interrupted by one or more oxo groups. Halogen may be chlorine, bromine, fluorine or iodine.

The oxacalixarenes of formula I are useful as adhesion promoting accelerators in alpha-cyanoacrylate compositions for bonding wood or other de-activating surfaces such as paper, leather, ceramic, plastics and metals with chromate-treated or acidic oxide surfaces. The inventive compositions are standard cyanoacrylate adhesive formulations to which have been added, as accelerators, calixarene compounds as defined above which are stable to cyanoacrylate monomers. The calixarene compounds are employed in amounts conventional for cyanoacrylate accelerators, preferably at levels between about 0.1% and 2% by weight of the composition.

The standard cyanoacrylate compositions are as described in U.S. Pat. No. 4,556,700 Harris et al at column 2, line 18 to column 3, line 32, the contents of which are incorporated herein by reference.

Oxacalixarene compounds may be readily synthesized by methods described in C. D. Gutsche, B. Dhawan, K. H. No and R. Muthukrishnan, J. Am. Chem. Soc. 103 p3782 (1981); B. Dhawan and C. D. Gutsche, J. Org. Chem. 48 p1536 (1983) and U.S. Pat. No. 4,098,717, R. Buriks, A. R. Fauke and F. E. Mange.

The present invention also relates to a method of producing etherified oxacalixarenes of formula I wherein a phenolic oxacalixarene is reacted with a halomethylketone or a haloalkyl acetate. Potassium iodide may be added to accelerate etherification.

The present invention also relates to cyanoacrylate adhesive compositions including as accelerator an oxacalixarene of formula I:

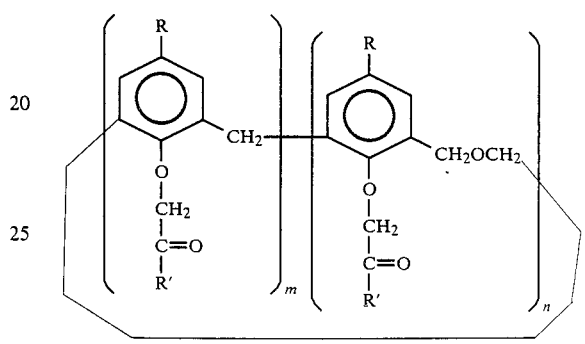

wherein m, n, R and R' are as defined above. Preferably the etherified oxacalixarene comprises from 0.1 to 5% by weight of the total adhesive composition.

DESCRIPTION OF THE PREFERRED EMBODIMENTS

The following Examples serve to illustrate the invention.

EXAMPLE 1

Preparation: The tetraethyl acetate of 7,13,19,25-tetra-tert-butyl-27,28,29,30-tetrahydroxy-2,3-dihomo-3-oxacalix-4-arene 7,13,19,25-tetra-tert-butyl 27,28,29,30-tetrahydroxy-2,3-dihomo-3-oxacalix-4-arene was prepared following the method of C. D. Gutsche, B. Dhawan, K. H. No, and R. Muthukrishnan, J. Am. Chem. Soc. 103 p 3782 1981 from p-tert-butylphenol paraformaldehyde and aqueous 5N potassium hydroxide in refluxing xylene. To 3.2 g of this compound (0.0047 mole) in 25 ml analar acetone was added 6.6 g (0.031 mole) ethyl bromoacetate and 4.2 g (0.030 mole) anhydrous potassium carbonate and the entire was refluxed under dry nitrogen with stirring for 120 hours. After this time all volatiles were removed including the excess ethyl bromoacetate under reduced pressure to give a buff coloured solid which was dissolved in 20 ml dichloromethane which was washed 3 times with 20 ml 10% aqueous $H_2SO_4$ and twice with 20 mls water. The separated dichloromethane layer was then dried over dried magnesium sulphate and volatiles were removed to give 4.0 g of product as a pale buff solid of yield 83%, which was chromatographed on acid-washed alumina and dichloromethane as eluent to give, following removal of volatiles, colourless solid tetraethyl acetate of 7,13,19,25-tetra-tert-butyl-27,28,29,30-tetrahydroxy-2,3-dihomo-3-oxacalix-4-arene m.pt. 63°–64° C., characterised by infra-red spectroscopy and elemental analysis.

I.R. Spectroscopy results: γ 1765 (S) cm$^{-1}$ C=O. Elemental analysis results (Calculated for $C_{61}H_{82}O_{13}$: C=71.59, H=8.08, O=20.34; Found: C=71.45, H=7.87, O=20.20).

EXAMPLE 2

Preparation: Tetraethyl acetate of 7,13,21,27-tetra-tert-butyl-29,30,31,32-tetrahydroxy-2,3,16,17-tetrahomo-3,17-dioxacalix-4-arene 7,13,21,27-tetra-tert-butyl-29,30,31,32-tetrahydroxy-2,3,16,17-tetrahomo-3,17-dioxacalix-4-arene was prepared by the thermally induced dehydration of 3-[3-hydroxymethyl)-5-tert-butylsalicyl]-5-tert-butyl-2-hydroxybenzyl alcohol, itself prepared from p-tert-butylphenol, formaldehyde and aqueous NaOH at 50° C. following the procedure of B. Dhawan and C. D. Gutsche J. Org. Chem. 48 (9) p. 1536 1983. To 0.5 g (0.0007 mole) 7,13,21,27-tetra-tert-butyl-29,30,31,32-tetrahydroxy-2,3,16,17-tetrahomo-3,17-dioxacalix-4-arene was added to 1.02 g (0.006 mole) ethyl bromoacetate and 0.65 g (0.0047 mole) anhydrous potassium carbonate and 10 mls analar acetone and the entire was refluxed under nitrogen with stirring for 120 hours. After this time all volatiles were removed including the excess ethyl bromoacetate under reduced pressure to give a buff-coloured sticky solid which was dissolved in 5 ml dichloromethane which was then washed 3 times with 5 ml 10% aqueous $H_2SO_4$ and then twice with 5 ml water. The separated dichloromethane was then dried over dried magnesium sulphate following which volatiles were removed to give 0.62 g product as a buff coloured solid of yield 74%. This solid was chromatographed on acid-washed alumina using dichloromethane as eluent to give the tetraethyl acetate of 7,13,21,27-tert-butyl-29,30,31,32-tetrahydroxy-2,3,16,17-tetrahomo-3,17-dioxacalix-4-arene as a colourless solid, m.pt. 211°–212° C. which was characterised by infra red spectroscopy and elemental analysis.

I.R. Spectroscopy results: γ 1760(S)cm$^{-1}$ C=O. Elemental Analysis: (Calculated for $C_{62}H_{84}O_{14}$: C=70.69, H=8.04, O=21.27; Found C=70.91, H=8.21, O=20.90).

EXAMPLE 3

Preparation: Triethyl Acetate of 7,15,23,-Tri-tert-butyl-2,3,10,11,18,19-hexahomo-3,11,19-trioxacalix-3-arene 7,15,23-Tri-tert-butyl-2,3,10,11,18,19-hexahomo-3,11,19-trioxacalix-3-arene was prepared by the thermally induced dehydration of 2,6-bis(hydroxymethyl)-4-tert-butylphenol (itself prepared from p-t-butylphenol, aqueous NaOH and formaldehyde solution, following U.S. Pat. No. 4,098,717, July 1978, by R. Buriks, A. Fauke and F. Mange of Petrolite Corporation) following the method of B. Dhawan and C. D. Gutsche in J. Org. Chem. 48(9) p. 1536 1983. 0.9 g (0.00117 mole) of this compound was added to 1.17 g (0.0070 mole) ethyl bromoacetate and 0.72 (0.0052 mole) anhydrous potassium carbonate and 10 mls analar acetone and the reaction mixture was refluxed with stirring under nitrogen for 120 hours. After cooling the reaction mixture was filtered and volatiles were removed from the filtrate under reduced pressure to give a pale yellow heavy oil which was taken up in 10 mls dichloromethane which was twice washed with 10 mls 5% aqueous $H_2SO_4$ and twice with 10 mls water. The dichloromethane layer was then dried with dried $MgSO_4$ and filtered and all volatiles were removed from the filtrate to give a pale yellow solid of product yield=1.23 g (94%), which was chromatographed on acid-washed alumina using dichloromethane as eluent to give the pure product as a colourless solid with a very sharp melting point m.pt. 45.5° C. confirmed as being the fully etherified tri(ethyl acetate) derivative of 7,15,23-Tri-tert-butyl-2,3,10,11;18,19-hexahomo-3,11,19-trioxacalix-3-arene by elemental and infra-red analysis.

I.R. Spectroscopy results: γ 1750 (S) cm$^{-1}$ C=O. Elemental Analysis: (Calculated for $C_{48}H_{66}O_{12}$: C=69.04, H=7.97, O=22.99; Found: C=67.66, H=7.96, O=22.16).

EXAMPLE 4

Ethyl cyanoacrylate stabilised with 10 ppm $BF_3$ was used as a base adhesive formulation. The additives shown below were dissolved in the base adhesive at the indicated level and fixture times on copy paper and white deal were determined. The results below demonstrate the good accelerative activity for these compounds.

|  |  | Fixture Time | |
| --- | --- | --- | --- |
| Additive | Amount | Copy Paper | White Deal |
| 0 | 0 | 60 seconds | 4–5 minutes |
| Example 1 | 1% | 5–10 seconds | 5–10 seconds |
| Example 2 | 1% | 15 seconds | 5–15 seconds |
| Example 3 | 1% | 30–40 seconds | 5 seconds |

We claim:

1. Oxacalixarenes of the general formula :

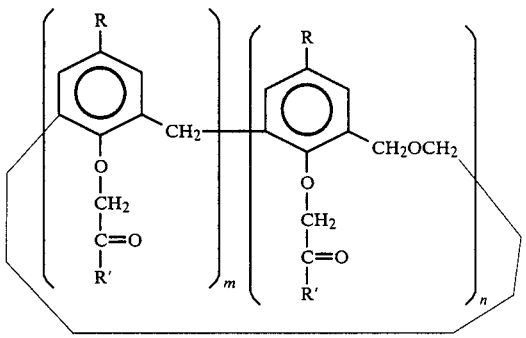

wherein m=0−7 and n=1−8 with the proviso that m+n<8;

R is hydrogen, halogen, or hydrocarbyl which may be substituted by one or more halo or oxo groups or interrupted by one or more oxo groups, and R may be the same or different on each aryl group; and R' is hydrocarbyl, which may be substituted by one or more halo or oxo groups or interrupted by one or more oxo groups, or hydrocarbyloxy, which may be substituted by one or more halo or oxo groups or interrupted by one or more oxo groups.

2. An oxacalixarene as claimed in claim 1 wherein hydrocarbyl is alkyl or alkenyl having 1 to 10 carbon atoms.

3. An oxacalixarene as claimed in claim 2 wherein hydrocarbyl is alkyl or alkenyl having 1 to 5 carbon atoms.

4. An oxacalixarene as claimed in claim 1 wherein halogen is chlorine, bromine or iodine.

5. An oxacalixarene as claimed in claim 1 which is an oxacalix-4-arene having the formula:

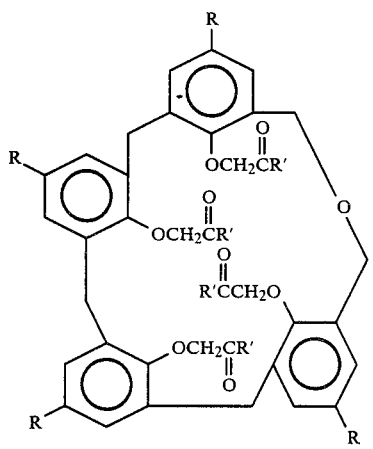

wherein R and R' are as defined in claim 1.

6. An oxacalixarene as claimed in claim 1 which is a dioxacalix-4-arene of formula:

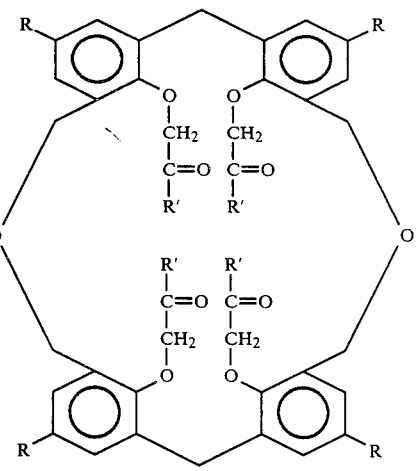

wherein R and R' are as defined in claim 1.

7. An oxacalixarene as claimed in claim 1 which is a trioxacalix-3-arene of formula:

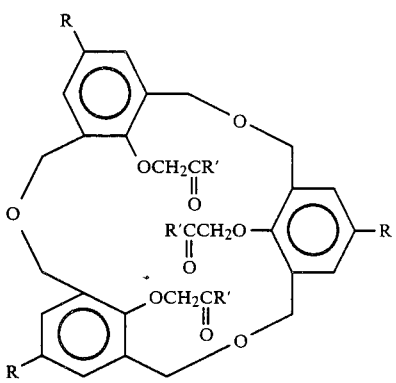

wherein R and R' are as defined in claim 1.

* * * * *

UNITED STATES PATENT OFFICE
CERTIFICATE OF CORRECTION

Patent No.     4,855,461     Dated     August 8, 1989

Inventor(s)     Harris, et al.

It is certified that error appears in the above-identified patent and that said Letters Patent is hereby corrected as shown below:

Front page, left column, Item [75] between "Harris" and "Dublin," insert -- and Maureen G. MacManus, both of --.

Signed and Sealed this

Ninth Day of October, 1990

*Attest:*

HARRY F. MANBECK, JR.

*Attesting Officer*     *Commissioner of Patents and Trademarks*

UNITED STATES PATENT OFFICE
CERTIFICATE OF CORRECTION

Patent No. 4,855,461        Dated August 8, 1989

Inventor(s)        Harris, et al.

It is certified that error appears in the above-identified patent and that said Letters Patent is hereby corrected as shown below:

At column 6, line 51, claim 1 which reads "$m + n < 8$" should read -- $m + n \leq 8$ --.

Signed and Sealed this

Third Day of September, 1991

*Attest:*

HARRY F. MANBECK, JR.

*Attesting Officer* — *Commissioner of Patents and Trademarks*